United States Patent
Charlez

(10) Patent No.: US 8,647,325 B2
(45) Date of Patent: Feb. 11, 2014

(54) CONNECTION DEVICE FOR MEDICAL USE

(75) Inventor: Jarl Charlez, Askim (SE)

(73) Assignee: Assut Europe S.p.A., Rome (IT)

(*) Notice: Subject to any disclaimer, the term of this patent is extended or adjusted under 35 U.S.C. 154(b) by 727 days.

(21) Appl. No.: 12/097,101

(22) PCT Filed: Dec. 18, 2006

(86) PCT No.: PCT/SE2006/050593
§ 371 (c)(1),
(2), (4) Date: Jun. 12, 2008

(87) PCT Pub. No.: WO2007/073336
PCT Pub. Date: Jun. 28, 2007

(65) Prior Publication Data
US 2008/0294146 A1   Nov. 27, 2008

(30) Foreign Application Priority Data
Dec. 19, 2005  (SE) ....................... 0502815

(51) Int. Cl.
*A61M 39/10*   (2006.01)
(52) U.S. Cl.
USPC ......................................... 604/533; 604/523
(58) Field of Classification Search
USPC ............... 604/523, 533, 534, 246, 256
See application file for complete search history.

(56) References Cited

U.S. PATENT DOCUMENTS

| | | |
|---|---|---|
| 4,900,068 A | 2/1990 | Law |
| 2003/0193190 A1 | 10/2003 | Werth |
| 2005/0251102 A1* | 11/2005 | Hegland et al. ............. 604/500 |

FOREIGN PATENT DOCUMENTS

| | | |
|---|---|---|
| FR | 2703593 A1 | 10/1994 |
| SE | 463 116 B | 10/1990 |
| WO | WO 96/37254 A2 | 11/1996 |

OTHER PUBLICATIONS

International Search Report of PCT/SE2006/050593, mailed Mar. 12, 2007.
Written Opinion of the International Searching Authority for PCT/SE2006/050593, mailed Mar. 12, 2007.

* cited by examiner

*Primary Examiner* — Bhisma Mehta
*Assistant Examiner* — Brandy S Lee
(74) *Attorney, Agent, or Firm* — Renner, Otto, Boisselle & Sklar, LLP

(57) ABSTRACT

A connection device for medical use, suitable to connect together biological and/or artificial liquid conveying structures, e.g. a blood vessel and a syringe, where one of the structures is provided with a first end and a lumen. The device is provided with a tubular portion with an insertion end which end is intended to be inserted in said lumen, and a sleeve, which is slideable along the tubular portion, and arranged to keep the vessel at the connection device.

9 Claims, 5 Drawing Sheets

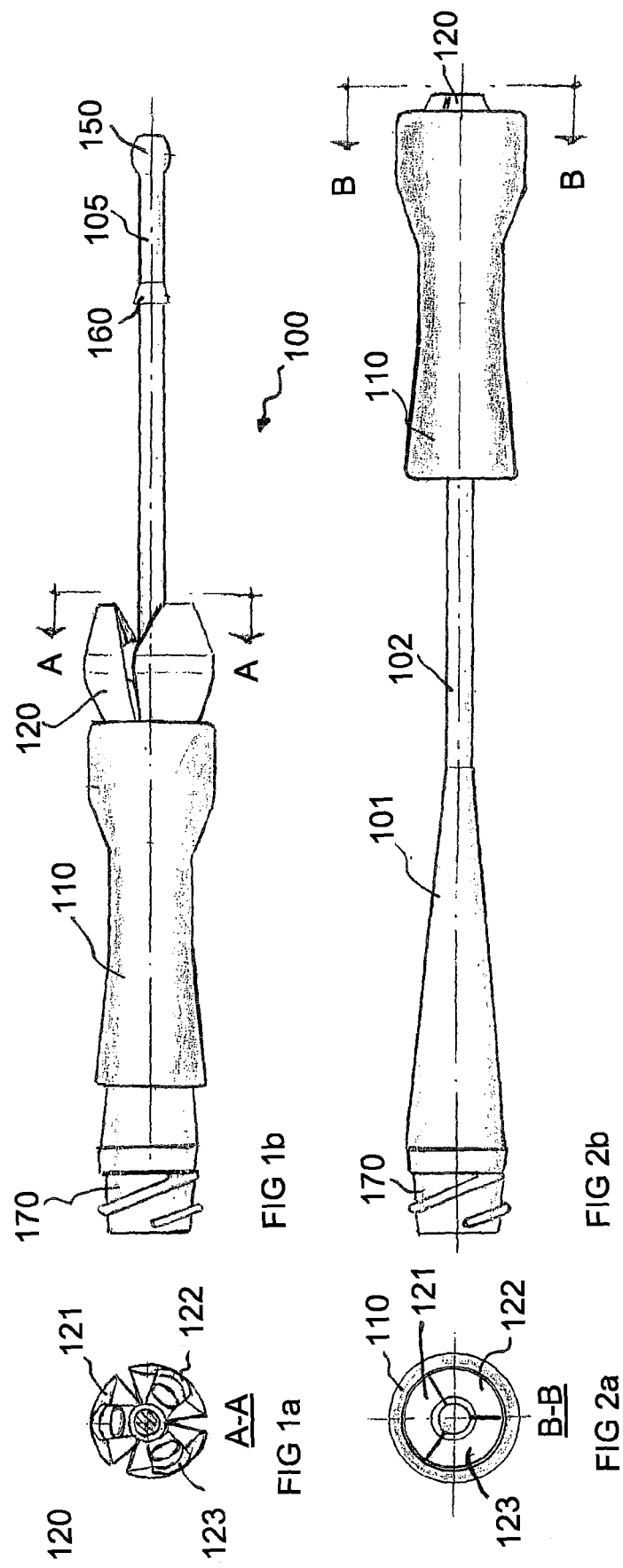

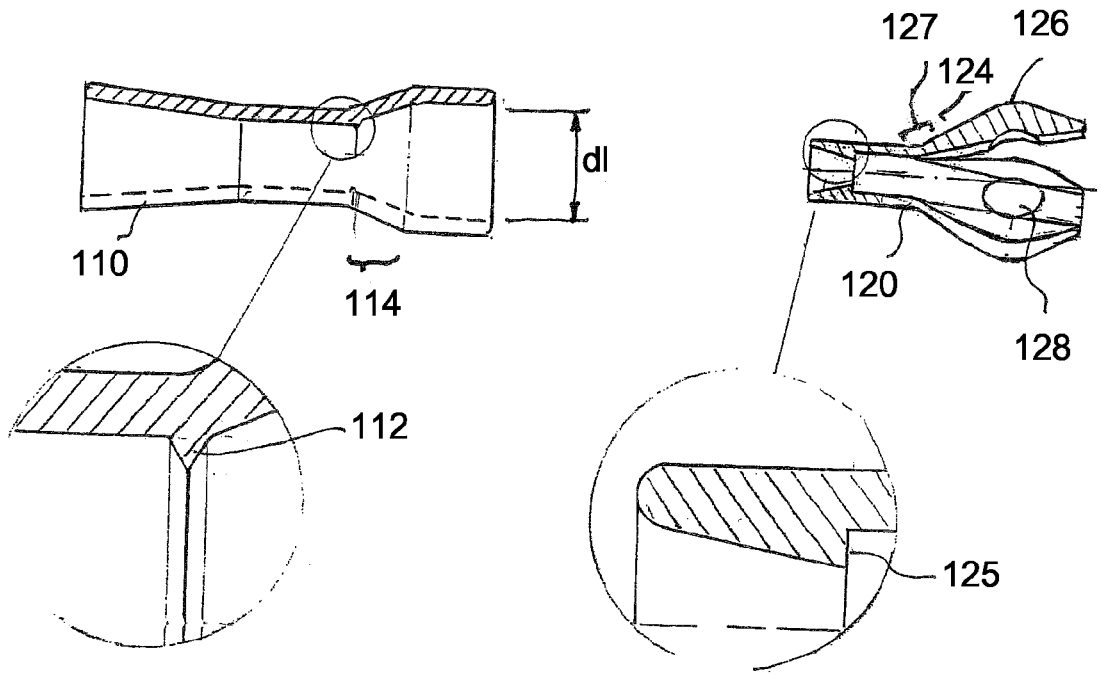
FIG. 4
FIG. 5
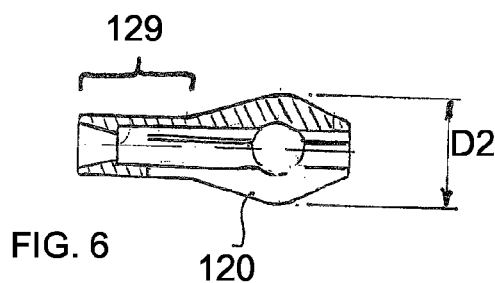
FIG. 6
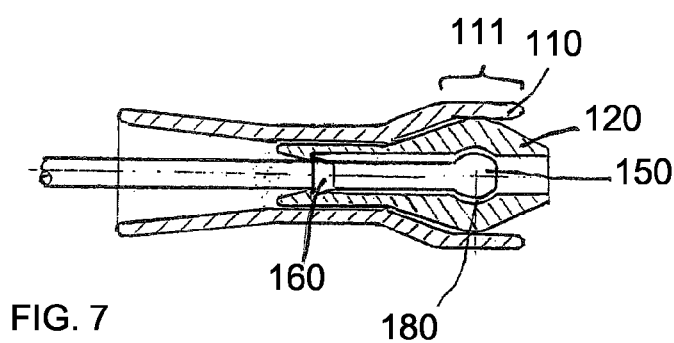
FIG. 7

CONNECTION DEVICE FOR MEDICAL USE

FIELD OF INVENTION

The present invention relates to the field of medical technology, in particular to devices for achieving a connection between a body vessel and a syringe or another liquid conveying device.

BACKGROUND OF THE INVENTION

Cardiovascular diseases are today treated by means of different methods. A widespread method comprises transplanting pieces of vessels from own or other people or even from animals between different places of the coronary vessels to achieve a by-pass of constricted portions, so-called coronary by-pass. During such surgical operations there sometimes arises a need for simply connecting a syringe to a piece of vessel.

SUMMARY OF THE INVENTION

The above-mentioned need is satisfied according to the present invention by a connection device for medical use which is suitable to connect biological and/or artificial liquid conveying structures, where one of the structures is provided with a first end and a lumen, where the connection device is provided with a tubular portion having an insertion end, which insertion end is intended to be inserted in said lumen, and a sleeve which is slideable along the tubular portion. The tubular portion is provided with a swelling in one of its ends.

The connection device is further provided with a chuck intended to contact a wall of said structure with a lumen, which can be a blood vessel provided with a vessel wall. The chuck is arranged slideable along the tubular portion. The chuck is shaped in such a way that when the insertion end of the tubular portion is arranged in said lumen the chuck can be slided along the tubular portion and contact said wall. The chuck is preferably adjusted in size on the outside to match the inside size of the sleeve, such that when the chuck is arranged to contact said vessel wall the sleeve can be slided along the tubular portion and the chuck, which is kept in place by a heel and a collar, can produce a pressure which keeps the vessel wall at the connection device.

The chuck is preferably provided with chuck jaws where at least one chuck jaw is provided with a recess which is adjusted to the swelling and to the thickness of said vessel wall.

The tubular portion is provided with a collar to prevent the chuck from falling off said portion, in particular when the sleeve is slided forward over the chuck. The sleeve is preferably provided with a ridge on its inside to produce friction against the cylindrical portion of the chuck.

In this way the chuck jaws will be closed when the sleeve is slided over the chuck, such that the inside of the sleeve cooperates with the outside of the chuck jaws and presses them together.

Further, a filling portion may be arranged on the insertion end close to the swelling. The filling portion confers to the insertion end an outer diameter in the same size as the inner diameter of the vessel that is to be connected along a distance of the insertion end, which corresponds to the distance on to which the vessel is brought over the insertion end, i.e. approximately up to the collar. The filling portion is preferably shaped in a resilient material.

Further, the invention provides a connection device of the above described kind, with the chuck being made of a tubular neck portion, which in one of its ends transforms to a chuck jaw portion, where chuck jaws are arranged and where a carrier structure of the chuck is arranged on the outside of the tubular neck portion to make contact with a corresponding carrier structure arranged on the inside of the sleeve to bring the chuck together with the sleeve, when the sleeve is slided over the chuck forward in the direction towards the swelling, and where the carrier structures are of a resilient design, such that they can give way when a force, which brings the sleeve forward in relation to the chuck, exceeds a certain magnitude. The carrier structure of the chuck is arranged over the neck portion at such a distance from the chuck jaw portion of the chuck that the carrier structure of the chuck cooperates with the carrier structure of the sleeve without having the front orifice of the sleeve making contact with the chuck jaws, but such that, when the friction between the respective carrier structures have been overcome and the sleeve has been brought past the position where the carrier structures cooperate, the front orifice of the sleeve can make contact with chuck jaws and press them together.

BRIEF DESCRIPTION OF THE DRAWINGS

The invention is described in the following with reference to the attached drawings of which:

FIGS. 1a and 1b show an overview over a connection device according to a first embodiment in a passive position.

FIGS. 2a and 2b show the connection device of FIG. 1 in a locked position.

FIG. 4 shows, partly in cross-section, a sleeve for the connection device of FIG. 1.

FIG. 5 shows, partly in cross-section, a chuck for the connection device of FIG. 1.

FIG. 6 shows, in cross-section, the chuck of FIG. 5 in closed position.

FIG. 7 shows the part, according to FIGS. 4 and 5, when the chuck is closed and locked position.

DETAILED DESCRIPTION OF PREFERRED EMBODIMENTS

Definitions

Figure 3:
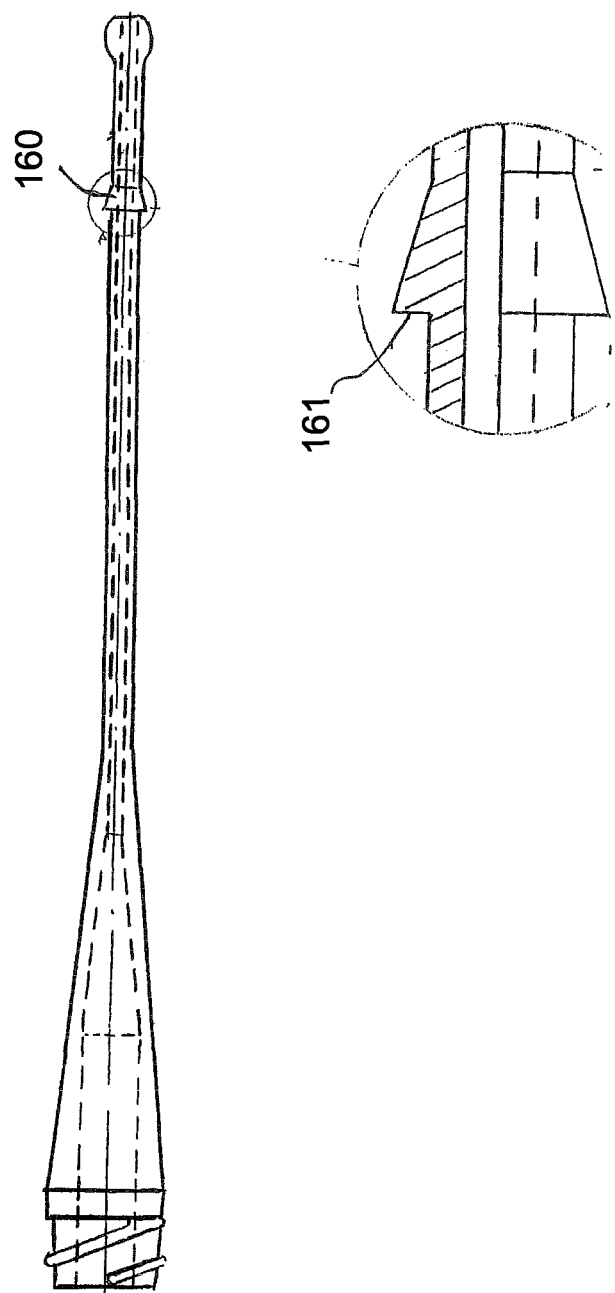
FIG. 3 shows a tubular base part for the connection device in FIG. 1.

With the concept "ridge" is in the present application meant one from an otherwise plane portion projecting structure or roughness having low altitude and width, but having in this context a length many times greater than the width.

The inventors have realized the need to be able to, at surgical operations, connect a liquid conveying device, e.g. a syringe, to a vessel or a vessel graft. At by-pass operations there may arise a need to measure the pressure and the flow in a vessel. It is then important that a connection between the pressure gauge and the vessel or vessel graft is able to resist the pressure, which is to be measured without loosening or leaking.

FIG. 1b shows a connection 100 provided with a tubular base part 101. The connection 100 is further provided with one, over the base part 101, slideable sleeve 110, and a vessel chuck 120. Also, the vessel chuck 120 is slideable along a portion 102 of uniform thickness of the base part 101. The base part 101 transforms in its first end to a standard connection 170, e.g. a Luer lock connection to connect the syringe or the like. The base part 101 is in its second end 150, its insertion end, provided with a vessel threading portion 105, preferably manufactured integral with said base part 101. The vessel threading portion 105 comprises a swelling in the shape of a bulb-shaped end portion 150, and a collar 160, arranged at a short distance from there.

A method to connect a blood vessel to said connection comprises the steps of:
- threading said vessel end over the swelling 150 on the vessel threading portion 105;
- sliding the sleeve 110 which frictionally connects with the chuck 120 over the vessel end until the chuck 120 is stopped in its movement by the stoppage of the heel 125 by the collar 160, where causing the friction between the sleeve and the chuck, due to the ridge 112, to be overcome.
- sliding the sleeve 110 further forward over the chuck 120, such that the front sleeve wall portion 111 presses towards a sloping plane 124 and further towards a crest 126 of each of the chuck jaws 121-123, which in turn will press towards the vessel wall and keep the vessel in position by squeezing it against the swelling 150.

FIG. 1a shows the chuck 120 as seen from the section A-A in FIG. 1b. The chuck is provided with three jaws 121, 122, 123.

FIG. 2b shows the connection 100 of FIG. 1b, where the chuck is in a closed and locked position. The chuck 120, slided to the vessel threading portion 105, vaguely seen under the sleeve 110.

FIG. 2a shows the chuck and the sleeve as seen from the section B-B of FIG. 2b.

FIG. 3 shows the tubular base part for the connection device of FIG. 1. In a detail view, partly in cross-section, it can be seen that the collar 160 is shaped as a straight frustum of a cone continuous with the portion of uniform thickness 102 at the thin end of the cone facing the swelling and forming a heel 161 at the thick end of the frustum.

FIG. 4 shows the sleeve 110 partly in cross section. The sleeve is provided with an opening towards the chuck 120, which opening has an inner diameter d1, which is so adjusted to the outer diameter D2 of the chuck, such that when a vessel is squeezed between the inner of the chuck and the swelling 150 on the base part 101, the sleeve will produce a tight pressure on the vessel wall. The sleeve is further provided with a conical portion on the inside 114, adjusted to the shape of the chuck.

The sleeve is preferably manufactured of a plastic material with a hardness roughly between 50-60 shore and the chuck of a material with a hardness of roughly 35 shore. The base part 101 is for example manufactured of a plastic material of nylon quality or of a metallic material.

The sleeve 110 is further in its inner provided with a ridge 112, arranged to increase the friction against the chuck 120, such that the chuck 120 will be brought together with the sleeve in an open position, when the sleeve is brought forward over the portion 102.

FIG. 5 shows the chuck 120 in an open position and with a detail enlargement showing a heel 125. A hinge joint zone 127 is arranged for each jaw 121, 122, 123. Further, each jaw is provided with a recess 128 to fit to the swelling 150 when a vessel wall is arranged in between. The heel 125 is preferably circularly arranged to brace against the collar 160. By this arrangement the sleeve and chuck can be moved forward over the tubular portion 102 of the base part 101 until the chuck 120 is stopped in its movement by the heel 125 which is stopped by the collar 160, and the friction between the sleeve and the chuck due to the ridge 112 can be overcome. The collar 160 and the heel 125 is arranged on such positions that the recess of the chuck 128 lands up substantially around the swelling 150.

FIG. 6 is a view, partly in cross-section, of the chuck 120 with outer diameter D2. In a preferred embodiment the chuck 120 is provided in one of its ends with a cylindric section 129 which frictionally contacts the ridge 112 of the sleeve 110, simultaneously as the inner diameter of the sleeve d1 makes frictional contact with a sloping plane 124 of one of each of the chuck jaws 121-123 and presses them down. The chuck can in alternative embodiments be provided with two, three or more jaws. Further, in further embodiments, the recesses 128 and/or the swelling 125 on its surface may be provided with small ribs or ridges, rifles or grooves, preferably of a soft shape to increase the friction against what is clamped, e.g. a vessel.

FIG. 7 is a view showing the swelling 150, the chuck 120, and the sleeve 110 in cooperation in a closed and locked position. The vessel is squeezed in a safe and pressure tight way in the space 180 between the swelling 150 and the recesses 128 in the chuck 120.

In an alternative embodiment there is no chuck. The sleeve 110 is arranged to squeeze a vessel wall directly against the swelling 150 and the sleeve is provided with a conicity on the inside at the end facing the swelling.

Figure 10:
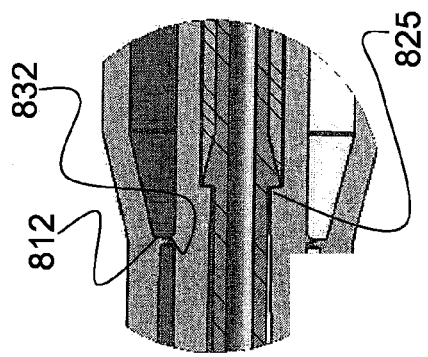
FIG. 10 shows a detail enlargement of an area J in FIG. 9.
Figure 8:
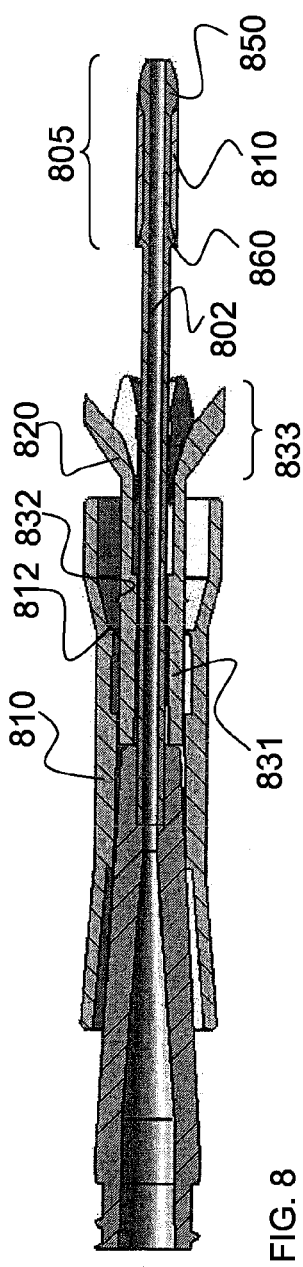
FIG. 8 shows, in longitudinal cross-section, a second embodiment of a connection device in a totally open position.
Figure 9:
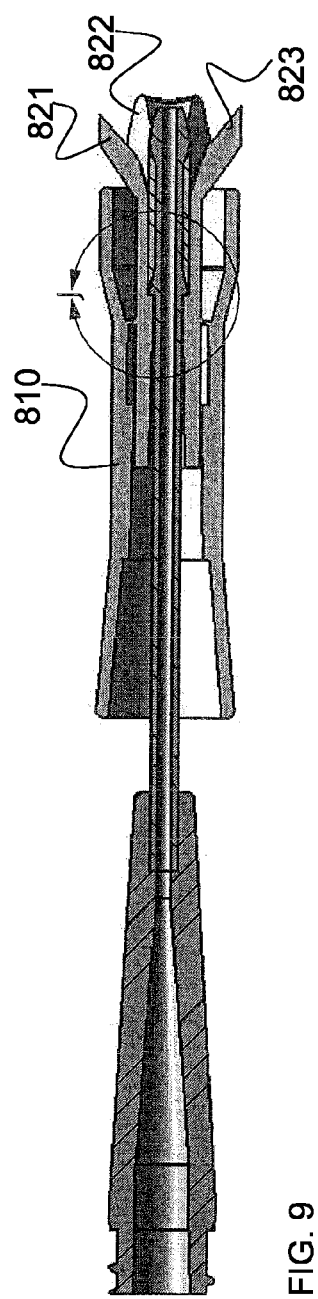
FIG. 9 shows the connection device, according to FIG. 8, in partially closed position with a chuck on its way forward.

FIG. 8 shows, in a longitudinal cross-section, further preferred embodiment of a connection device in a totally open position. The vessel threading portion 805 of the connection device differs from the embodiment, described above, in that close to a swelling 850, preferably between the swelling 850, and a collar 860, arranged on a distance from the swelling, is arranged a filling portion 810, preferably of a resilient material. The filling portion 810 is arranged to prevent the vessel, which is to be connected, from hanging down and interfere with the chuck 820, when the chuck in open position is brought forward along the tubular portion 802. The filling portion may be concentric and massive or give support only in small number of points. The chuck comprises a tubular neck portion 831 in one end of which chuck jaws are arranged by letting the tubular shape split and transform into chuck jaws. A carrier structure, preferably shaped as a circumferential ridge 832 is arranged on the neck portion 831 of the chuck at a distance from the chuck jaw portion 833 over the chuck 820, such that the sleeve 810 brings the chuck 820 due to frictional contact between a carrying structure 812 of the inside of the sleeve, preferably in the shape of the ridge 812, and the ridge 822 of the chuck 820, when the sleeve is moved forward in the direction towards the vessel threading portion 805 without letting the front opening of the sleeve make contact with the chuck jaws, see FIGS. 9 and 10.

When the sleeve 810 has carried the chuck 820 to a position, where a preferably circumferential stop heel 825, arranged on the inside of the neck portion of the chuck, is stopped by the collar 860, the friction between the ridge 822 of the chuck 820 and the ridge 812 of the sleeve is overcome and the sleeve can be moved further forward and close and lock the preferably three jaws 821, 822, 832 of the chuck 820. The heel 825 is arranged at such a distance from the chuck jaw portion that when it cooperates with the collar, the swelling lands opposite the jaws. The jaws of the chuck is manufactured such that they normally stay totally open. The chuck is manufactured in a material as described above which allows them to flex in the transition between the neck portion of the chuck and the chuck jaw portion 833 of the chuck, when the sleeve 810 presses them down. The chuck and the ridge of the chuck is preferably manufactured of somewhat softer material than the sleeve and the ridge of the sleeve.

Figure 12:
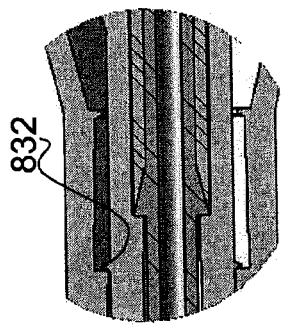
FIG. 12 shows a detail enlargement of an area B in FIG. 11.
Figure 11:
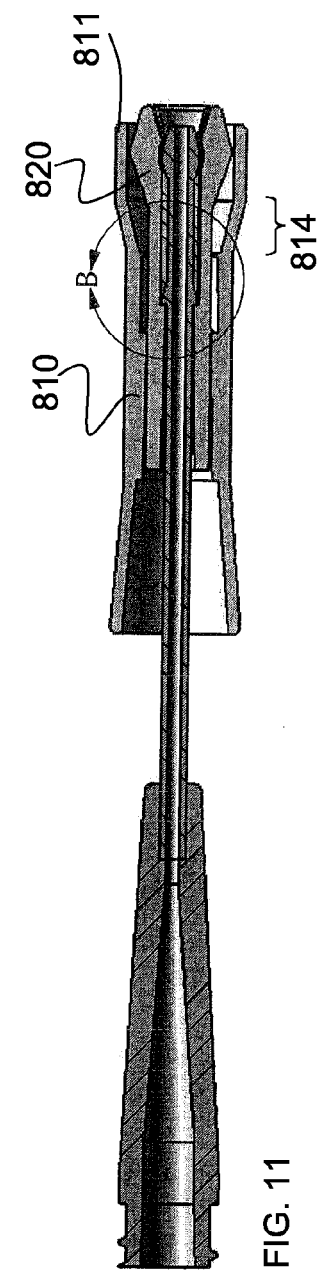
FIG. 11 shows the connection device, according to FIG. 8, in a totally closed position.

FIGS. 11 and 12 show the connection device with a closed and locked chuck, where the ridge 832 of the chuck can be used to prevent that the sleeve 812 is moved so far forward over the chuck 820 that the pressure on the squeezed vessel increases more than intended due to unintended contact with the conical portion 814 of the sleeve 810. Normal closing of the chuck is achieved by letting the inner side of a front portion 811 of the sleeve wall press towards the outside of jaws 821, 822, 823, when the sleeve is brought forward over the chuck in the same way as described above. The carrier structure 112 of the sleeve 812, may also be a bulge, which may be circumferential or partially circumferential of the inner circumference of the sleeve. The carrying structure of the sleeve is preferably arranged close to a portion of the sleeve which is conically widened and intended to house the chuck portion of the chuck, when the chuck is in a closed and locked position.

The carrying structure 832 of the chuck may also be a bulge, which can be circumferentially running or partially circumferentially running around the outer circumference of the neck portion of the chuck. The carrying structure of the chuck is arranged at a distance from the chuck portion of the chuck, which is such that when the carrying structure of the chuck cooperates with the carrying structure of the sleeve, the open chuck jaws are in the vicinity of or just outside the extension of the sleeve, such that they avoid being pressed together by said sleeve.

Figure 13:
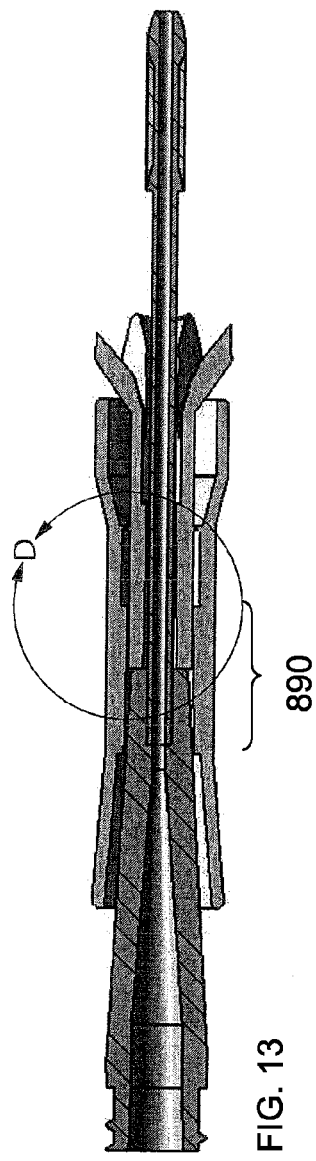
FIG. 13 shows the connection device, according to FIG. 8, in a partially open position.

Another advantage is that the inner diameter of a middle portion 890 of the sleeve 810 has been arranged to fit with relatively small play against the neck portion 831 of the chuck, which gives rigidity to the design, confer FIG. 13.

Figure 14:
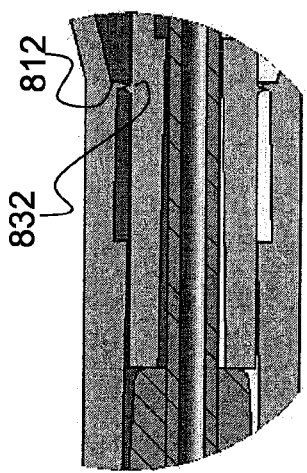
FIG. 14 shows a detail enlargement of an area D in FIG. 13.

Further, FIG. 13 and FIG. 14 show how the chuck after having been opened by bringing the sleeve somewhat backwards, further carried by the sleeve when the ridge 812 of the sleeve once again has come into contact with the ridge 832 of the chuck. At least one of the ridges should be circumferential to keep contact despite relative rotation between the sleeve 810 and the chuck 820. An advantage with this, is that the chuck jaws 821, 822, 823 of the chuck 820 can be removed from the vessel in an easy way and particularly without having the surgeon to use his fingers or some surgical instrument.

Both the connection of the vessel and the disconnection of the vessel are procedures that due to the design of the connection device are much more gentle to the vessel in question. The vessel will therefore survive a connection. It is also a fact that former methods to suture a syringe to the vessel entailed that 1-1.5 cm of the vessel had to be cut away due to the fact that the sutures simply could not be untightened. This cutaway is not necessary using the connection device according to the invention, which increases the supply of usable vessel material.

The invention claimed is:

1. A vessel connection device for medical use suitable to connect together a body vessel and a liquid conveying device, where said body vessel has a first end, a lumen and a vessel wall defining said lumen, where the connection device comprises a tubular portion with an insertion end including a swelling for insertion into said lumen and a sleeve, slideable along the tubular portion, wherein a chuck, arranged at the tubular portion, which can be in an open and in a closed position and intended to squeeze said body vessel with a lumen, arranged over the insertion end and the swelling between itself and said swelling, and wherein that said chuck can be locked in a closed position by means of a sliding of said sleeve along said tubular portion; wherein the sleeve is provided with a conicicity on the inside, intended to close the chuck when sliding the sleeve; wherein the chuck is so shaped that when the insertion end of the tubular portion is arranged inside said lumen, the chuck is able to move over the tubular portion, contacting the wall, which defines said lumen; wherein said chuck is adjusted in size on its outside to the inside size of the sleeve, such that when the chuck is brought into contact with the wall, the sleeve can be slid along the tubular portion and produce a pressure which maintains contact between the vessel wall and the connection device; and wherein said chuck is provided with chuck jaws, and where at least one chuck jaw is provided with a recess configured to accommodate the swelling and the thickness of the vessel wall.

2. The connection device according to claim 1, where said sleeve is arranged to lock said chuck in a closed position, when it is moved in a direction from a base part of said connection towards said insertion end.

3. The connection device according to claim 1, where said chuck is slidably arranged along the tubular portion.

4. The connection device according to claim 1, wherein said tubular portion is provided with a collar, intended to stop the movement of the chuck along the portion at a certain position.

5. The connection device according to claim 4, wherein said sleeve on its inside is provided with a ridge, intended to cause friction between the sleeve and the chuck.

6. The connection device according to claim 1, where said chuck is provided with three or more chuck jaws.

7. The connection device according to claim 1, where a filling portion is arranged in the vicinity of said swelling to prevent said body vessel from hanging down and interfering with the movement of the chuck.

8. The connection device according to claim 1, where the chuck comprises a tubular neck portion which at one end transforms into a chuck jaw, wherein a carrying structure of the chuck is arranged on the outside of the tubular neck portion to make contact with a corresponding carrying structure arranged on the inside of the sleeve to bring the chuck together with the sleeve, when the sleeve is slid forward over the chuck in the direction towards the swelling, and where the carrying structures are of a resilient design such that they can give way when a force which brings the sleeve forward in relation to the chuck reaches a certain magnitude.

9. The connection device according to claim 8, where the carrying structure of the chuck is arranged on the neck portion at such a distance from the chuck jaw portion of the chuck that the carrying structure of the chuck cooperates with the carrying structure of the sleeve without the front opening of the sleeve making contact with the chuck jaws, but such that when the friction between the carrying structures have been overcome, and the sleeve has been brought past the position where the carrying structures cooperate, the front opening of the sleeve can make contact with the chuck jaws.

* * * * *